(12) United States Patent
Shadduck

(10) Patent No.: US 7,651,685 B2
(45) Date of Patent: Jan. 26, 2010

(54) USE OF MICROCHIMERIC CELLS IN THE TREATMENT OF MALIGNANCY

(76) Inventor: Richard K. Shadduck, 915 Settlers Ridge Rd., Pittsburgh, PA (US) 15238

( * ) Notice: Subject to any disclaimer, the term of this patent is extended or adjusted under 35 U.S.C. 154(b) by 299 days.

(21) Appl. No.: 11/483,972

(22) Filed: Jul. 10, 2006

(65) Prior Publication Data

US 2007/0020246 A1    Jan. 25, 2007

Related U.S. Application Data

(60) Provisional application No. 60/697,873, filed on Jul. 8, 2005.

(51) Int. Cl.
*A01K 35/14*     (2006.01)
*G01N 33/48*    (2006.01)

(52) U.S. Cl. .................. 424/93.71; 424/534; 436/63

(58) Field of Classification Search ................. None
See application file for complete search history.

(56) References Cited

U.S. PATENT DOCUMENTS

2003/0190306 A1    10/2003   Kuroiwa et al.

OTHER PUBLICATIONS

Ochiai et al (Bone Marrow Transplantation, 2002, vol. 30, pp. 793-796).*
Shimazaki et al (Blood, 2003, vol. 101, pp. 3334-3336).*
Ichinohe et al (Blood, 2004, vol. 104, pp. 3821-3828).*
Ueno et al (Blood, 2003, vol. 102, pp. 3829-3836).*
Umeda K. et al., "Successful T-cell-replete peripheral blood stem cell transplantation from HLA-haploidentical microchimeric mother to daughter with refractory acute lymphoblastic leukemia using reduced-intensity conditioning" Bone Marrow Transplantation (2003), vol. 31, No. 11, pp. 1061-1063.
Ishida H. et al., "Non-T-cell depleted HLA-Haploidentical hemotopoietic stem cell transplantation from a family donor based on fetomaternal microchimerism in pediatric hematologic malignancies" J Pediatr Hematol Oncol (2003), vol. 26, No. 1, pp. 68-71.
Gilmore et al., Fetal-Maternal Microchimerism: Basis For A Potential New Therapy For Malignancy?, Abstract, Blood, 2004.
Gilmore et al., Does Fetal-Maternal Microchimerism Confer Immunologic Tolerance Of Fetal Cells?, Abstract, International Society of Experimental Hematology, Abstract, 2005.
Gilmore et al., Does Fetal-Maternal Microchimerism Confer Immunologic Tolerance Of Fetal Cells?, Poster, Meeting of the International Society of Experimental Hematology, 2005.
Gilmore et al., Fetal-Maternal Microchimerism: A Potential Novel Approach For Treating Malignancy?, Abstract, American Society of Clinical,Oncology, Abstract, 2005.
Gilmore et al., Incidence Of Fetal-Maternal Microchimerism in Parous Cancer Patients., Abstract, International Society of Experimental Hematology, Abstract, 2006.
Gilmore et al., Incidence Of Fetal-Maternal Microchimerism in Parous Cancer Patients., Poster, Meeting of the International Society of Experimental Hematology, Abstract, 2006.
Gilmore et al., Effect Of Chemotherapy Treatment On Fetal-Maternal Microchimerism In Parous Cancer Patients., Abstract, Blood, 2006.

* cited by examiner

*Primary Examiner*—Karen A Canella
(74) *Attorney, Agent, or Firm*—Reed Smith LLP

(57) ABSTRACT

Methods and formulations for the treatment of malignancies. Assessment of the incidence and scope of MC in control and cancer populations provides for the development of cellular therapy approaches to hematologic malignancies that are expected to be well tolerated immunologically. Studies will confirm that parous females who display MC are able to tolerate donor cells from their male offspring immunologically. Studies will explore the use of MC offspring donor cells in cellular therapy for the treatment of hematologic and other malignancies.

25 Claims, 5 Drawing Sheets

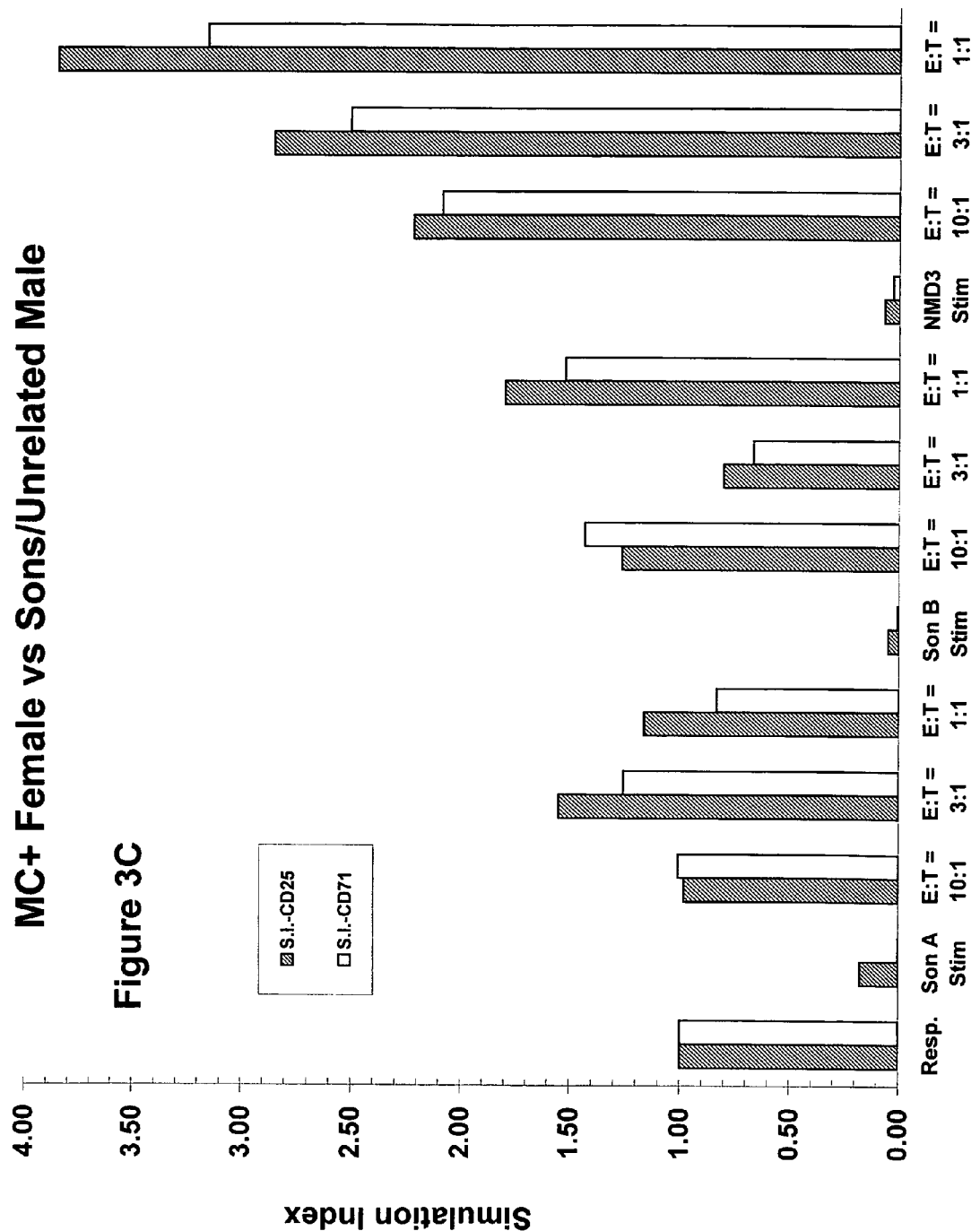

USE OF MICROCHIMERIC CELLS IN THE TREATMENT OF MALIGNANCY

CROSS-REFERENCE TO RELATED APPLICATION

This application claims the benefit under 35 U.S.C. §119 (e) of the earlier filing date of U.S. Provisional Application Ser. No. 60/697,873 filed on Jul. 8, 2005.

BACKGROUND OF THE INVENTION

1. Field of the Invention

The present invention relates to methods of treating malignancy by employing microchimeric cells. Initial studies confirm the presence of microchimeric cells in parous cancer patients. Assessment of immunotolerance and son-to-mother cellular therapy are also evaluated and discussed. Cellular therapeutic administration of male offspring cells to the microchimeric mother is also discussed.

2. Description of the Background

Microchimerism is defined as the presence of two genetically distinct populations of cells, one population being a much lower concentration, in the same individual or organ. In the case of fetal-maternal microchimerism (MC), cells are thought to traffic between the fetal circulation and the maternal circulation via the placenta. The presence of cells from the fetus in the mother persists for decades post-partum. The traditionally-reported incidence of MC is 33% in normal parous women with a sensitivity of 1 male cell/$10^6$ female cells. However, the incidence and extent of MC among normal females and female cancer patients has not been fully investigated.

Hematologic malignancies such as leukemia and lymphoma are cancers of the blood system that often develop in the bone marrow. Traditionally, treatment of hematologic malignancies involve chemotherapy potentially coupled with blood and bone marrow transplants. Alternatively, suspensions of cells may be administered to the patient in a process called cellular therapy. One consistent difficulty encountered in tissue transplants and cellular therapy is possibility of immunological rejection of the newly-introduced cells by the host. A long standing need has been felt by the medical community for the ability to treat malignancies via transplantation or cellular therapy, while at the same time reducing the risk of immunological rejection by the host. The present invention addresses these outstanding needs.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF THE INVENTION

Figure 1A:
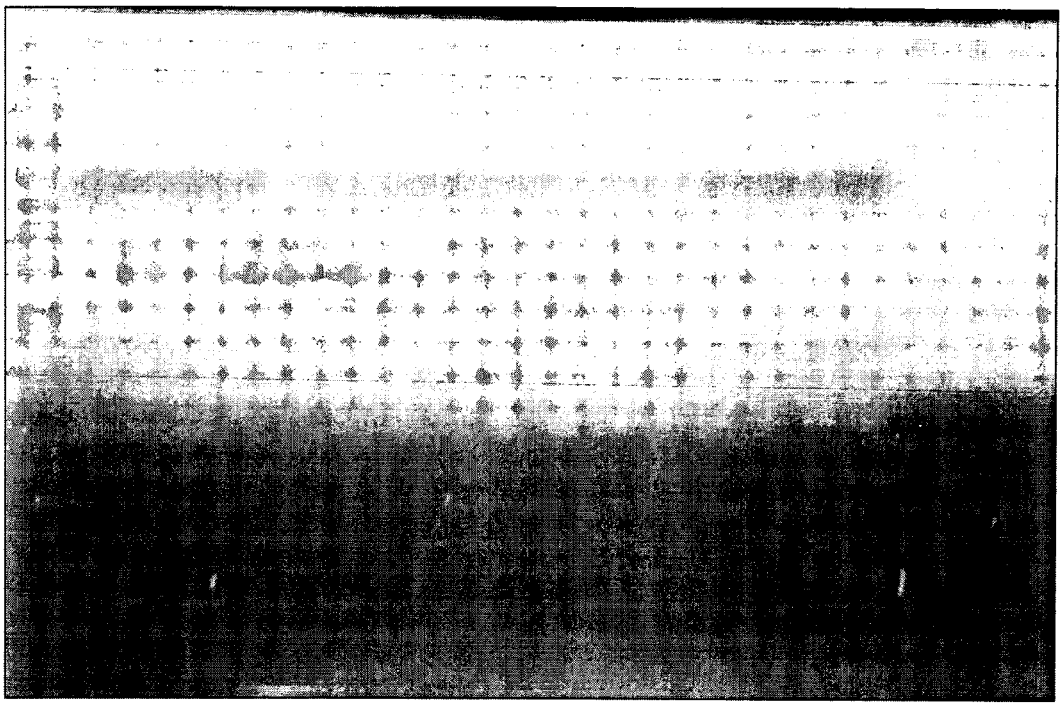
FIG. 1 displays scans of two gels that confirm the presence of MC cells in control parous population and confirm the lack of MC in non-parous population.

It is to be understood that the figures and descriptions of the present invention have been simplified to illustrate elements that are relevant for a clear understanding of the invention. The detailed description will be provided hereinbelow with reference to the attached drawings.

The present invention relates to the development of methods and formulations for the treatment of malignancies. The implementation of the present invention with respect to the treatment of hematologic malignancies will be particularly discussed. However, that discussion should not be considered limiting as the present invention has application in the treatment of all malignancies. Assessment of the incidence and scope of MC in control and cancer populations provides for the development of cellular therapy approaches to hematologic malignancies that are expected to be well tolerated immunologically. Studies will confirm that parous females who display MC are able to tolerate donor cells from their male offspring immunologically. Studies will explore the use of MC offspring donor cells in cellular therapy for the treatment of hematologic malignancies.

Initially, studies were performed to evaluate the actual frequency of MC in parous females. Studies were also conducted to assess whether the frequency of MC increases when higher levels of cells are assayed. Using the data from control subjects as a benchmark, the frequency of MC in parous female cancer patients was measured.

After obtaining informed consent from normal parous and non-parous female donors and female cancer patients, approximately 32 milliliters of blood was collected in four tubes containing sodium citrate anticoagulant from BECTON-DICKINSON. Samples were spun at 1,500×g for 20 minutes to allow mononuclear cell separation, according to the manufacturer's instructions. The interface containing the mononuclear cells was collected and diluted in Isolex Working Buffer (Dulbecco's phosphate buffered saline/1% human serum albumin/0.4% sodium citrate), then centrifuged at 300×g for 10 minutes to pellet the cells. The pellet was suspended in 10 milliliters working buffer, and a 0.1 milliliter sample was taken for a mononuclear cell count.

DNA was isolated from mononuclear cell preparations using QIAamp Blood DNA Miniprep kit (QIAGEN) according to the manufacturer's instructions, with a maximum input cell number of $5 \times 10^7$ per preparation. DNA concentration and purity was determined by measuring $A_{260\,nm}$ and $A_{280\,nm}$ of a 1:50 dilution of the final product.

One microgram of each DNA preparation was quality control tested for polymerase chain reaction (PCR) using beta-globin primers with AmpliTaq Gene-Amp reagents (Perkin-Elmer); 30 cycles. A 10 microliter sample of the reaction was mixed with agarose gel sample buffer and electrophoresed in 2% agarose in Tris-borate buffer containing 10 microgram/milliliter ethidium bromide. Bands were visualized and photographed on a UV trans-illuminator.

Initially, triplicate 1 microgram samples of each DNA preparation was subjected to two rounds of PCR for a human Y chromosome-specific sequence using nested sets of primers. Reactions included 1 microliter Perfect Match Enhancer (STRATAGENE). After the initial amplification of 40 cycles, 2 microliters of the primary reaction was transferred to a secondary reaction tube containing the internal set of Y chromosome-specific primers and amplified 25 cycles. Y chromosome-specific bands were visualized in agarose gels as above. Human cell lines were obtained from ATCC and were used as controls—K562 (ATCC # CCL 243) as a negative control DNA (female) and KG-1 (ATCC # CCL 246) as positive control DNA (male). To test the sensitivity of the assay, serial dilutions of male KG-1 cells were mixed with female K562 cells in ratios of 1:10, 1:100, 1:1,000, 1:10,000, 1:100,000, 1:1,000,000 and 1:10,000,000. DNA was prepared from each dilution, quality control tested, and run in the Y chromosome-specific PCR as above. That test established the sensitivity of the MC assay at 1:1,000,000. A sample of this mixture was included in each subsequent assay as a MC control, along with K562, KG-1, and no DNA controls.

The populations of subjects for the initial experiments included 200 normal parous subjects with a median age of 48.8±9.3 years with a range of 27-71. The average number of male children was 1.5±0.7 with a range of 1-4. Samples were also collected from 54 normal non-parous women, who had a median age of 38.6±10.1 years with a range of 23-63. Samples were also collected from 200 cancer patients, who had a median age of 61.7±12.5 years, with a range of 27-90. Their average number of male children was 1.8±1.0, with a range of 1-5. The diagnoses for these patients included multiple myeloma (14), leukemia (21), colorectal cancer (22) lymphoma (24), breast cancer (37) uterine cancer (19), ovarian cancer (17), lung cancer (24), cervical cancer (10) and a variety of miscellaneous malignancies (22). The mononuclear cell yields were slightly lower in cancer patients [mean of 20±25.7 million cells versus 23±12.7 million cells for normal parous subjects] and the average DNA yields were about 67% of that obtained from normal parous subjects (27.7±50 μg (microgram) versus 41±19.3 μg).

Figure 1B:
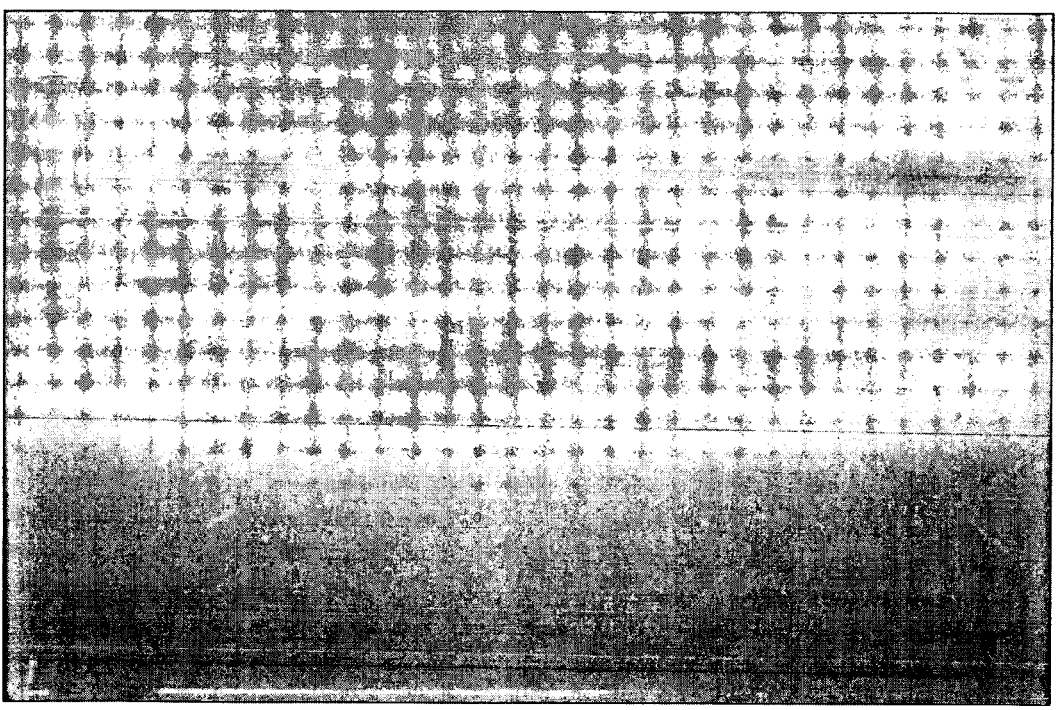

FIG. 1 shows electrophoresis gels demonstrating the presence of male DNA in parous normal and cancer patients. Lane 1 shows a 100 base pair DNA ladder, lane 2 is a control lane that includes only water and no DNA, Lane 3 has DNA extracted from the KG-1 (male) cell line, lane 4 has DNA extracted from K562 (female) cell line, and Lane 5 has a 1:1,000,000 dilution of DNA from KG1/K562 as an MC control. FIG. 1A Lanes 6-17 show DNA from normal parous control patients. In FIG. 1B, lanes 1-5 are the same as FIG. 1A. Lanes 6-19 display DNA from non-parous control. Those data demonstrate the ability to measure MC in clinical populations.

Figure 2:
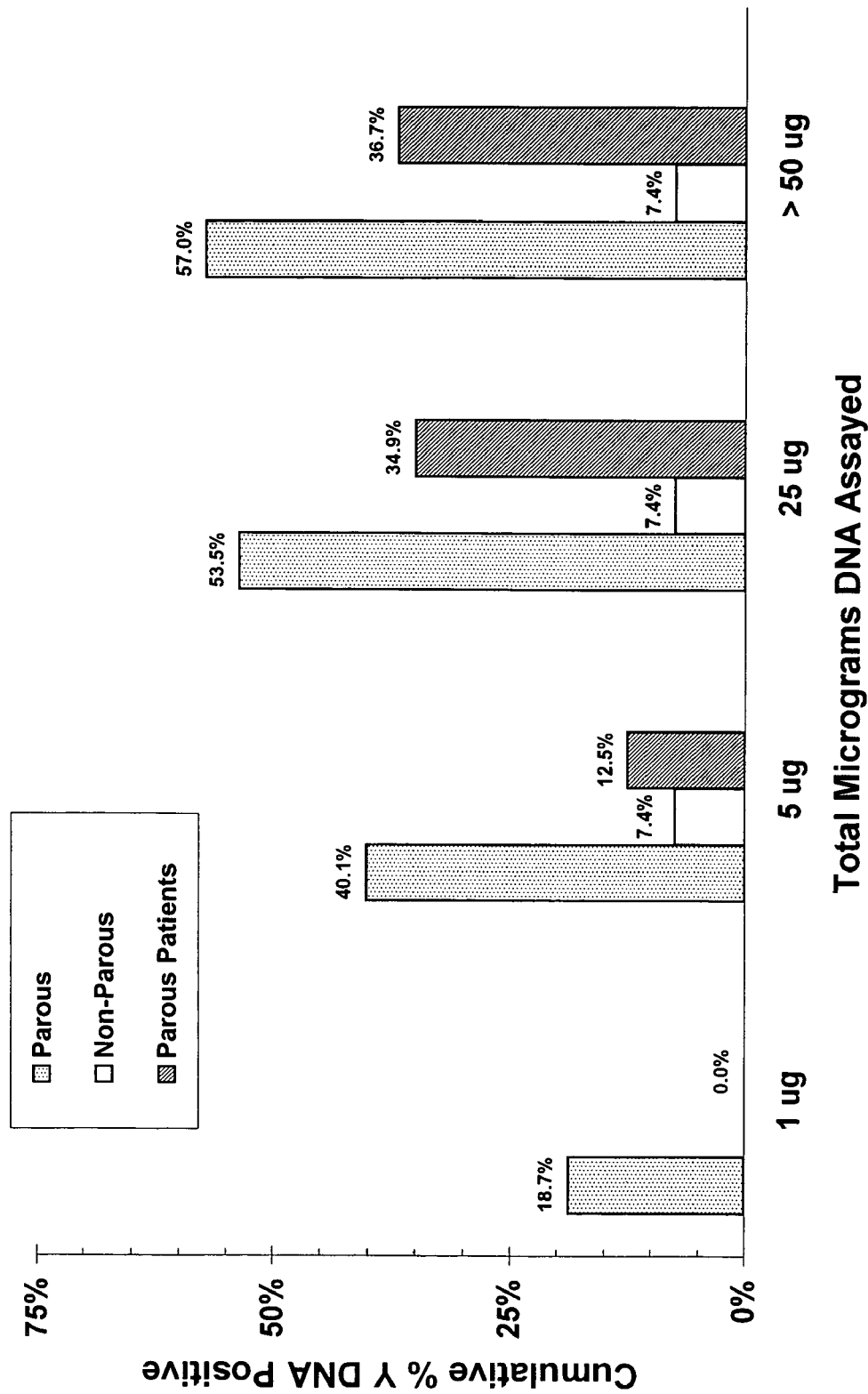
FIG. 2 depicts population data demonstrating the presence of MC in parous, non-parous, and parous cancer subjects.

FIG. 2 displays the population data collected to test the incidence and extent of MC in normal and cancer patient populations. The observed frequency was dependent on the amount of DNA assayed. With 1 μg DNA (~300,000 genomes) per test, the frequency of MC was 18%. At 5 μg DNA (1.5 million genomes), the level rose to 40%, and at ≧25 μg DNA (7.5 million genomes), 57% of normal parous women had MC. Among cancer patients, MC was present in 12.5% with 5 μg, and rose to 36.7% when ≧25 μg was tested. This level is lower than that of the normal parous subjects, which likely reflect the cumulative effect of chemotherapy toxicity on the MC population of cells. One interesting result is that 47% of patients with hematologic malignancies had MC, but only 28% of solid tumor patients were MC. The exact reason for this finding is unclear, but it may be related to the types of chemotherapeutic agents used for treating the different types of cancer. An unexpected finding was that 4 out of 54 non-parous subjects were also MC (7.4%), a finding that has been independently reported by routine screening of blood bank samples Yan Z, Lambert N C, Guthrie K A, et al. 2005. "Male microchimerism in women without sons: Quantitative Assessment and correlation with pregnancy history." *American Journal of Medicine*, 118, 889-906.

Thus confirming the presence of MC in the cancer patient population, further investigations will assess immunological tolerance in MC females for cells derived from their offspring. Cells will be isolated from the male offspring for introduction in the MC mother. Mononuclear cell preparations are isolated as detailed as above using BECTON-DICKINSON Leukaprep CPT tubes. MNC preparations from sons and unrelated male donors are inactivated by mitomycin C as described below, and used as stimulators in mixed-lymphocyte culture (MLC). Untreated MNC from the mother are cocultured with the inactivated MNC from the sons and unrelated male donor for one week and the cultures are harvested for flow cytometric analysis of expression of the T-lymphocyte activation markers, CD25 (IL-2 receptor beta chain) and CD71 (transferrin receptor). A culture of maternal MNC without stimulators serves as a negative control and the cocculture of maternal MNC on inactivated unrelated male donor MNC serves as a positive control from the MLC response. Absence of response against a son's MNC indicates immune tolerance of that son's cells.

MLC:MNC preparations from sons and unrelated male donors are inactivated by incubating the cells in the presence of 25 micrograms per milliliter mitomycin C in Dulbecco's phosphate-buffered saline (pH-7.4) for 30 minutes at 37° C. The mitomycin-inactivated cells are washed four times with Isolex Working Buffer (Item 10), resuspended to $5 \times 10^6$ cells per milliliter in R+10 medium, which is RPMI-1640 (GIBCO/INVITROGEN) containing 10% fetal calf cerum and 1% antibiotic/anti-mycotic solution (GIBCO/INVITROGEN). These inactivated MNC cells serve as stimulators for maternal MNC which are the responders in MLC.

The MNC preparation from the mother is resuspended in R+10 at a cellular concentration of 5×106 cells per milliliter. A volume of 0.1 milliliter of responders are added to the wells of a 24 well culture plate and graded doses of each stimulator MNC preparation are added; standard effector:target (E:T) ratios are 1:1, 3:1, 10:1, and 30:1. R+10 culture medium is added to bring each well to 0.5 milliliter total volume. For these cultures, the number of stimulator cells in the different wells changes and the number of responder cells is kept constant. One well per stimulator population contains only stimulators and one well per culture plate contains only responders to control for assay background. The culture plate is maintained for seven days at 37° C. in 5% CO2 and is fed at day three or day four with 0.5 milliliter R+10 medium.

After seven days, the culture is harvested. A volume of 0.1 milliliters of the culture is subjected to a cell count and the remaining cells are split into three aliquots. One aliquot is stained with antibodies to human CD25, CD3, and CD45; the second with antibodies to CD71, CD3, and CD45 to quantify the percent of human T lymphocytes expressing either CD25 or CD71. The third aliquot of cells is stained with isotype control antibodies. By comparing the degree of activation and the total lymphocyte expansion of each culture well, the reactivity of the mother's lymphocytes against both her son's lymphocytes and unrelated male lymphocytes may be assessed. If the mother's lymphocytes respond to the unrelated male cells but not against the son's cells, then immunologic tolerance would be demonstrated. The immunological results will be correlated with the MC state of the mother based on the DNA-based MC assay described above to determine if MC does indeed confer immunologic tolerance of the son's cells.

Figure 3:
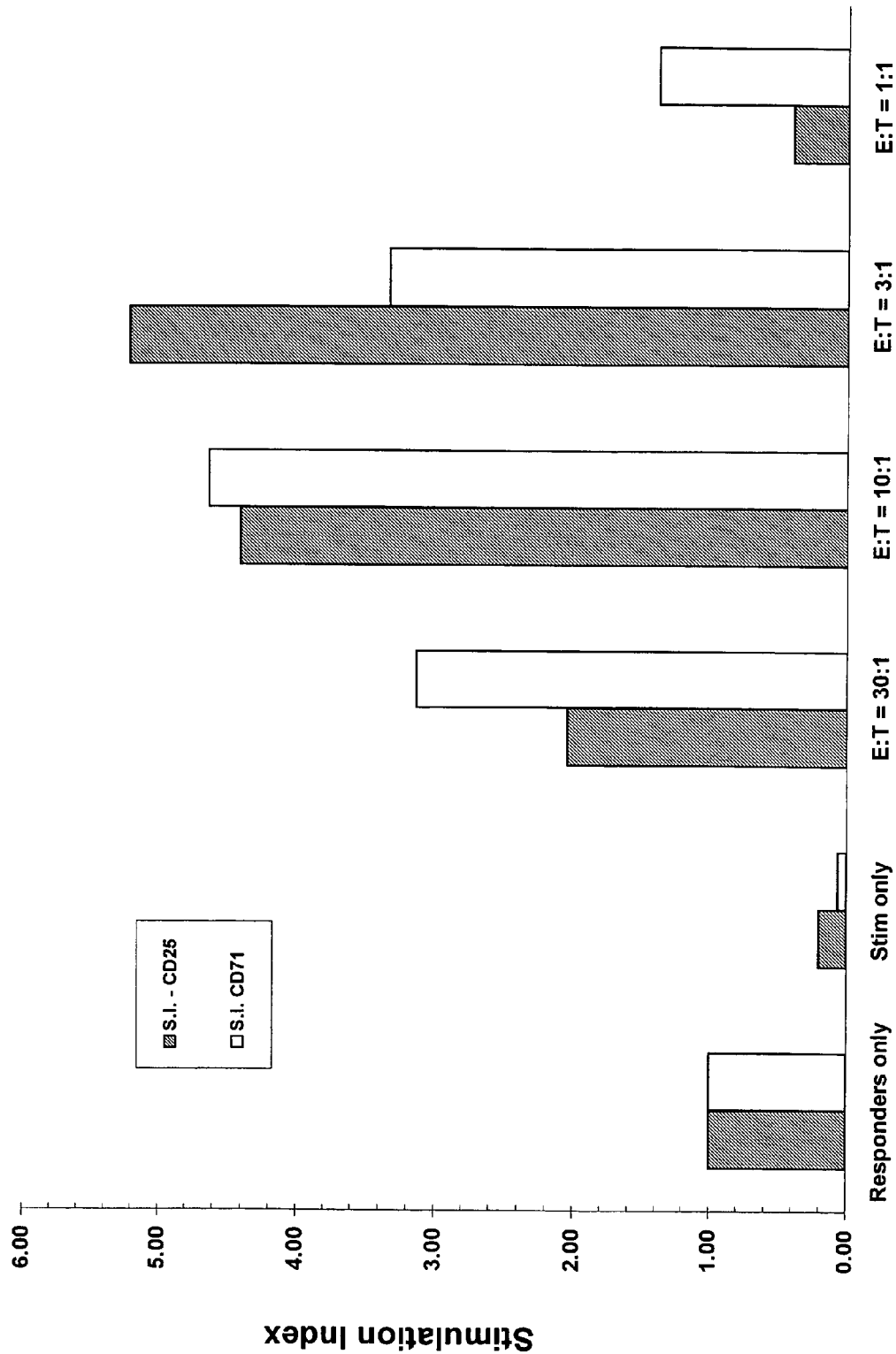
FIG. 3 shows the results of immunological MLC experiments with lymphocyte preparations.
Figure 3B:
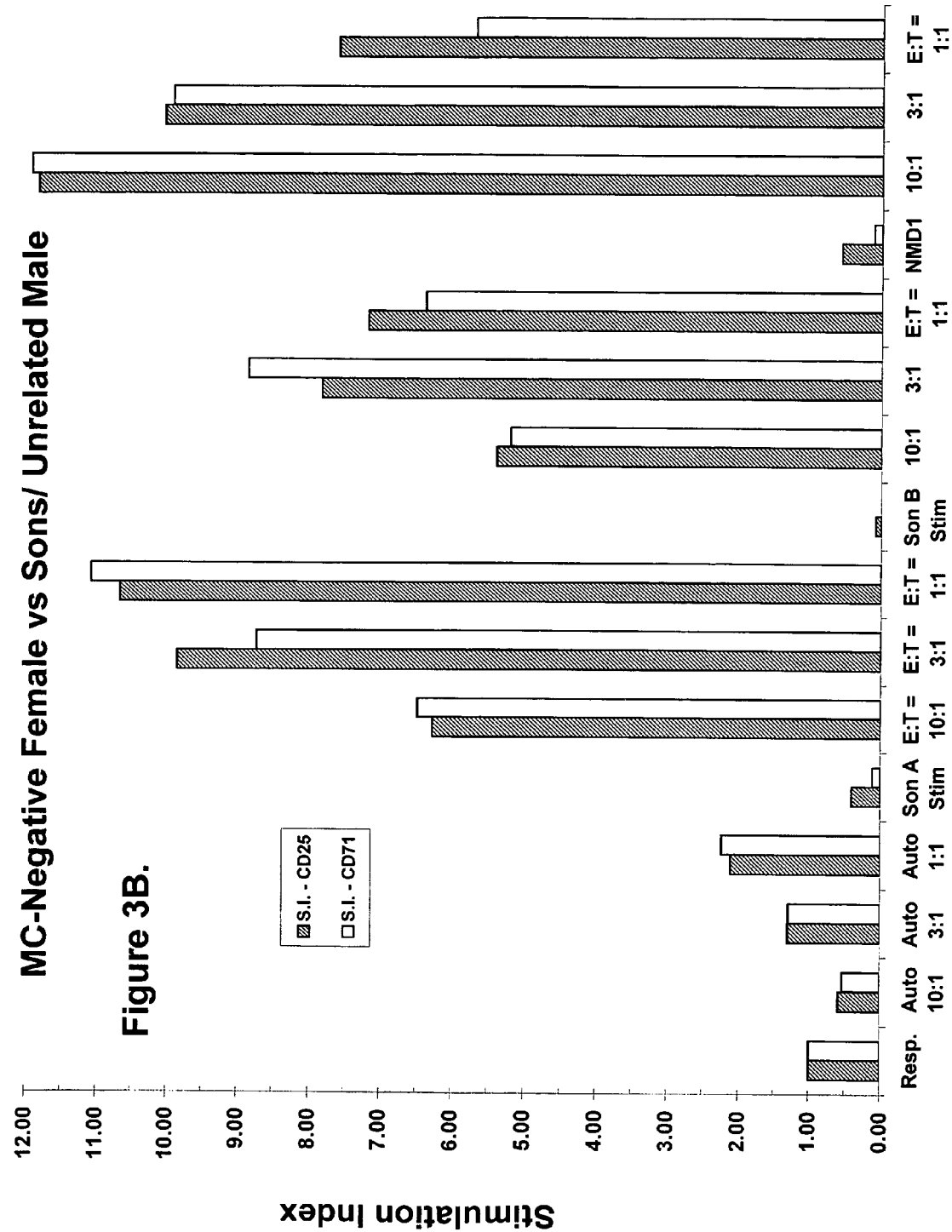

FIG. 3 shows the results of 3 MLC experiments. Panel A shows the reaction of non-parous female responder lymphocytes against mitomycin-treated stimulator lymphocytes from an unrelated male donor at different Effector-to-Target (E:T) ratios. The results are expressed in terms of Stimulation Index (S.I.) where $$S.I. = \frac{(\% \, CD25 \text{ or } CD71 \text{ positive cells})_{culture} - (\% \, CD25 \text{ or } CD71 \text{ positive cells})_{control}}{(\% \, CD25 \text{ or } CD71 \text{ positive cells})_{control}}$$

Panel B shows the reaction of responder lymphocytes from a MC-negative mother against mitomycin-treated stimulator lymphocytes from 2 of her sons and an unrelated male donor. Panel C shows the lack of reaction of responder lymphocytes from a MC-positive mother against mitomycin-treated stimulator lymphocytes from 2 of her sons, while retaining reactivity against mitomycin-treated stimulator lymphocytes from an unrelated male donor. These results support the contention that MC renders the mother's immune system tolerant to her son's cells.

Additional clinical experiments will establish the effectiveness of the present invention in the treatment of malignancies. In one presently-preferred embodiment, a clinical protocol will be employed in which cells from an MC are son are obtained, analyzed, and infused into the mother who has a malignancy that can be evaluated for response after lymphocyte infusion. After identifying the appropriate donor, that individual will under go a complete history and physical examination as well as tests for infectious disease markers. Assuming that the laboratory values are correct, the donor will undergo leukophoresis over a 3-4 hour time period in which approximately 12 liters of cells are processed on a Baxter CS 3000 machine. Ordinarily, that procedure can be accomplished using peripheral venous access. Approximately $10^{10}$ cells (of which 70-80% are lymphocytes) are obtained by that procedure.

After obtaining the cells, the sample will be analyzed by cell count and by flow cytometry using antibodies to CD3 as well as various T-cell subsets. Those cells will then be infused intravenously into the recipient with the malignant disease. The first step will be to determine the survival of the infused T cells. That will be done by standard MC analysis for the Y chromosome at intervals of 1, 3, 6, and 24 hours after infusion. Subsequently, blood will be obtained twice weekly for the next two weeks to determine the redistribution and survival of the infused cells. The kinetic study should provide some information as to the acceptance of the cells and their potential redistribution.

In addition, patients will be evaluated for any potential untoward effects from the infusion. That could include fever, chills, or tachycardia, although such effects are unlikely. A late effect might be the potential development of graft-versus-host disease, which is manifested by skin rash, abdominal pain, cramps, diarrhea, and/or elevation of liver function tests, particularly the alkaline phosphatase and gamma GTP. Those tests will be observed weekly over the next 30 days following cellular infusion.

The patient will also be evaluated for any potential beneficial effects. Measurements of the tumor and/or the malignancy, such as leukemia, will be evaluated using standard techniques. Patients will be evaluated weekly at the same time they are assessed for any potential development of graft-versus-host disease. In some circumstances, patients will be evaluated every week for 2 months after donor lymphocyte infusion (DLI) for evidence of response and graft-versus-host disease, followed by evaluation every 2 months for 6 months, every 6 months for 2 years, and then annually thereafter. Those individuals with tumors that are not readily accessible to examination will have appropriate x-rays or scans obtained at regular intervals to determine any beneficial effects.

If there is sufficient survival of the chimeric T cells, but an insufficient response in terms of large numbers of circulating cells or in terms of a response of the patient's disease, the next group of patients will be given a much larger volume of cells. Several techniques have been described for the expansion of T cells including one that employs immobilized antibodies to CD3 and CD28 on microbeads.

Additional work will be performed to arrange for the expansion of the donor T cells through one of several available methods. Preferably, an approximate 200-fold expansion of T cells is obtained. Those T cells will be administered as described hereinabove with unexpanded cells. In order to provide a margin of safety, in some preferred embodiments 90% of the cell expansion will be frozen under controlled conditions using liquid nitrogen. In the same preferred embodiments, the remaining 10% will be administered immediately with similar kinetic studies to be performed over the subsequent weeks, also as described hereinabove. If no unwanted side effects are observed, the remaining 90% of the expanded cells will be infused and a kinetic study will be performed. In other preferred embodiments, the percentage of the cell expansion that is administered to patients will be varied according to the effectiveness of the treatment or the amplitude of the desired effect.

Detailed observations of the patients will be undertaken and any potential response of the underlying malignancy will be evaluated. Liquid (i.e., blood tumors) tumors will be evaluated by standard oncological techniques. Solid tumor response will be characterized by RECIST criteria. Response of hematologic malignancies will be characterized by standard response criteria for each type of cancer (i.e., for CML: hematologic or cytogenetic response, with the latter being further described as minor [<67% $Ph^+$ cells by FISH], major [<33% $Ph^+$ cells], or complete [0% $Ph^+$ cells]). If any patients develop symptoms of graft-versus-host disease, they will be treated with immunosuppressive therapy using corticosteroids, tacrolimus, and mycophenolate mofetil. Additional immunosuppressive drugs will be readily known to those of skill in the art and are entirely appropriate for use within the context of the present invention.

The techniques described herein for use in MC-based cellular therapy may be used in conjunction with more traditional cancer treatments. For example, patients may be treated using chemotherapy, resection, transplantation, or radiation approaches either before, during, or after MC-based cellular therapy. The specific traditional treatment to be used will be determined by the type and severity of the cancer being treated. The specific parameters of MC cell administration (i.e., concentration of cells, dosing regimen, etc.) will be determined readily by one of ordinary skill in the art.

It will be appreciated by those skilled in the art that the invention may be practiced within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses or adaptations of the inventions following, in general, the principles of the invention and including such departures from the present disclosure as come within known or customary practice within the art to which the invention pertains.

What is claimed is:

1. A method of treating a parous patient who is suffering from a malignancy, comprising the steps of:
    verifying that said patient exhibits fetal-maternal microchimerism;

obtaining a leukopheresis sample from a donor who is an offspring of said patient, wherein the sample includes HLA-mismatched leukocytes with respect to the patient and HLA-matched leukocytes with respect to the microchimeric cells within the patient, and wherein said leukopheresis sample comprises T cells;

expanding said T-cells; and administering said expanded T cells or a portion of said expanded T cells to said patient.

2. The method of claim 1, wherein said malignancy is a malignancy of the blood.

3. The method of claim 1, wherein said malignancy is a solid tumor.

4. The method of claim 1, further comprising assessing effects of said administering step on said malignancy.

5. The method of claim 1, further comprising administering at least one immunosuppressive drug to said patient.

6. The method of claim 5, wherein said immunosuppressive drug is selected from the group consisting of corticosteroids, tacrolimus, and mycophenolate mofetil.

7. A method of treating a parous patient who is suffering from a malignancy, comprising the steps of:

combining microchimerism-based (MC-based) cellular therapy with radiation therapy, resection, or chemotherapy, wherein said MC-based cellular therapy comprises the steps of:

verifying that said patient exhibits fetal-maternal microchimerism;

obtaining a leukopheresis sample from a donor who is an offspring of said patient, wherein the sample includes HLA-mismatched leukocytes with respect to the patient and HLA-matched leukocytes with respect to the microchimeric cells within the patient, and wherein said leukopheresis sample comprises T cells;

expanding said T-cells; and administering said expanded T cells or a portion of said expanded T cells to said patient.

8. The method of claim 7, wherein said malignancy is a malignancy of the blood.

9. The method of claim 7, wherein said malignancy is a solid tumor.

10. The method of claim 9, further comprising administering at least one immunosuppressive drug to said patient.

11. The method of claim 10, wherein said immunosuppressive drug is selected from the group consisting of corticosteroids, tacrolimus, and mycophenolate mofetil.

12. A method of treating a parous patient who is suffering from a malignancy, comprising the steps of:

verifying that said patient exhibits fetal-maternal microchimerism;

obtaining a leukopheresis sample from a donor who is an offspring of said patient, wherein said sample includes HLA-mismatched leukocytes with respect to the patient and HLA-matched leukocytes with respect to the microchimeric cells within the patient, wherein said leukopheresis sample comprises approximately $10^{10}$ cells of which 70-80% are lymphocytes comprising T cells; and administering said leukopheresis sample or a portion of said leukopheresis sample to said patient.

13. The method of claim 12, wherein said malignancy is a malignancy of the blood.

14. The method of claim 12, wherein said malignancy is a solid tumor.

15. The method of claim 12, further comprising assessing effects of said administering step on said malignancy.

16. The method of claim 12, further comprising expanding said T-cells prior to said administering step.

17. The method of claim 12, further comprising administering at least one immunosuppressive drug to said patient.

18. The method of claim 17, wherein said immunosuppressive drug is selected from the group consisting of corticosteroids, tacrolimus, and mycophenolate mofetil.

19. A method of treating a parous patient who is suffering from a malignancy, comprising the steps of:

combining MC-based cellular therapy with radiation therapy, resection, or chemotherapy, wherein said MC-based cellular therapy comprises the steps of:

verifying that said patient exhibits fetal-maternal microchimerism;

obtaining a leukopheresis sample from a donor who is an offspring, wherein said sample includes HLA-mismatched leukocytes with respect to the patient and HLA-matched leukocytes with respect to the microchimeric cells within the patient, wherein said leukopheresis sample comprises approximately $10^{10}$ cells of which 70-80% are lymphocytes comprising T cells; and administering said leukopheresis sample or a portion of said leukopheresis sample to said patient.

20. The method of claim 19, wherein said malignancy is a malignancy of the blood.

21. The method of claim 19, wherein said malignancy is a solid tumor.

22. The method of claim 21, further comprising administering at least one immunosuppressive drug to said patient.

23. The method of claim 22, wherein said immunosuppressive drug is selected from the group consisting of corticosteroids, tacrolimus, and mycophenolate mofetil.

24. The method of claim 19, further comprising isolating T cells from said leukopheresis sample.

25. The method of claim 24, further comprising expanding said T cells prior to said administering step.

* * * * *